United States Patent [19]

Davis

[11] Patent Number: 4,545,146

[45] Date of Patent: Oct. 8, 1985

[54] ROUTE TO HYBRID SOYBEAN PRODUCTION

[75] Inventor: William H. Davis, Hale Center, Tex.

[73] Assignee: Ring Around Products, Inc., Dallas, Tex.

[21] Appl. No.: 585,940

[22] Filed: Mar. 5, 1984

[51] Int. Cl.$^4$ .............................................. A01H 1/02
[52] U.S. Cl. .................................... 47/58; 47/DIG. 1
[58] Field of Search ............................. 47/58, DIG. 1

[56] References Cited

U.S. PATENT DOCUMENTS 3,903,645  9/1975  Bradner .
4,077,157  3/1978  Bradner .
4,517,763  5/1985  Beversdorf et al. ................... 47/58

OTHER PUBLICATIONS

"A Partially Male Sterile Strain of Soybeans," by C. E. Caviness, H. J. Walters and D. L. Johnson, Crop Science, vol. 10, pp. 107–108, (Jan.–Feb. 1970).
"Inheritence of a Male-Sterile Character in Soybeans," by C. A. Brim and M. F. Young, Crop Science, vol. 11, pp. 564–566, (Jul.–Aug. 1971).
"Influence of Temperature on a Partially Male-Sterile Soybean Strain," by C. E. Caviness and B. L. Fagala, Crop Science, vol. 13, pp. 503–504, (Sep.–Oct. 1973).
"Implications of Male-Sterility in Soybeans", by A. Brim, Proceedings of the Sixth Soybean Seed Research Conference–1976, pp. 67–71.
"Technology of Hybrid Soybeans", by W. H. Davis, Proceedings of the Sixth Soybean Seed Research Conference–1976, pp. 72–74.
"A New Male-Sterile Strain in Wabash Soybeans", by H. K. Chaudhari and W. H. Davis, J. of Heredity, vol. 68, pp. 266–267, (1977).
"Pollen Production in Soybeans with Respect to Genotype, Environment, and Stamen Position", by R. G. Palmer, M. C. Albertson and H. Heer, Euphytica, vol. 27, pp. 427–433, (1978).
"Genetics and Cytology of the $ms_3$ Male-Sterile Soybean", by R. G. Palmer, C. W. Johns and P. S. Muir, J. of Heredity, vol. 71, pp. 343–348, (1980).
"Pollination of Male-Sterile Soybeans in Caged Plots", by P. D. Koelling, W. J. Kenworthy and D. M. Caron, Crop Science, vol. 21, pp. 559–561, (Jul.–Aug. 1981).
"Variable Development in Anthers of Partially Male-Sterile Soybeans", by D. M. Stelly and R. G. Palmer, J. of Heredity, vol. 73, pp. 101–108, (1982).
"Genetics and Cytology of the $ms_4$ Male-Sterile Soybean", by X. Delanney and R. G. Palmer, J. of Heredity, vol. 73, pp. 219–223, (1982).
"Application of Genetic Male Sterility to Recurrent Selection Schemes in Soybeans" by C. A. Brim and C. W. Stuber, Crop Science, vol. 13, pp. 528–530, Sep.–Oct., 1973.
"Genetics and Ultrastructure of a Cytoplasmically Inherited Yellow Mutant in Soybeans" by Reid G. Palmer and Peter N. Mascia, Genetics 95, pp. 985–1000, Aug. 1980.

*Primary Examiner*—Robert E. Bagwill
*Attorney, Agent, or Firm*—Burns, Doane, Swecker & Mathis

[57] ABSTRACT

An improved procedure for forming $F_1$ hybrid soybean plants (i.e., hybrid soybean plants of the first filial generation) is provided which is capable of being readily implemented on a commercial scale. Unlike processes proposed in the prior art the requisite cross-pollination needed to produce the $F_1$ hybrid having hybrid vigor is precisely controlled. The seed parent upon which seeds capable of forming $F_1$ hybrid plants are produced is fully male sterile (as described herein) thereby eliminating the possibility of self-pollination. It surprisingly has been found that the required male sterility is made possible in the seed parent by combining via a controlled plant breeding program previously widely dispersed factors comprising an atypical Cms cytoplasm and two distinct pairs of recessive genes for fertility restoration $r_1r_1$ and $r_2r_2$. For instance, the Cms cytoplasm conveniently may be derived from a Mandarin cytoplasmic source (e.g., the Elf variety), the $r_1r_1$ recessive genes conveniently may be derived from a Dunfield germplasm base (e.g. the Bedford variety), and the $r_2r_2$ recessive genes conveniently may be derived from a Tokyo germplasm base (e.g., the Braxton variety).

86 Claims, No Drawings

ROUTE TO HYBRID SOYBEAN PRODUCTION

BACKGROUND OF THE INVENTION

It is well known that when different plant lines are cross-pollinated one can achieve in the offspring a highly desirable heterosis or hybrid vigor which advantageously provides increased yields of the desired crop.

Representative crops which have been successfully hybridized in the past include sugar beets, corn (See U.S. Pat. No. 3,753,663 to Jones), sorghum, alfalfa (See U.S. Pat. No. 3,570,181 to Davis), wheat, sunflowers, cotton, rice (See U.S. Pat. No. 4,305,225 to Yuan), cucumbers, onions, carrots, and tomatoes.

Soybeans (i.e., seeds of *Glycine max* plants) are recognized to be an important crop in many parts of the world. For instance, approximately 65 to 75 million acres of soybeans are planted annually in the United States which establishes this to be the largest seed crop presently grown in the United States. However, in spite of research by many skilled plant scientists over the past 50+ years, soybeans represent the last major seed crop which is not being grown by the farmer in a hybridized form. Accordingly, the farmer heretofore has not had available seed capable of growing hybrid soybean plants which exhibit a vigor which is attributable to the crossing of two diverse parent lines.

As reported in *Modern Soybean Production*, by Walter O. Scott and Samuel R. Aldrich, published by The Farm Quarterly, Cincinnati, Ohio 45210 in 1970:

"The secret of producing hybrid soybean seed on a commercial scale is yet to be discovered."

As indicated by B. B. Singh in "High Frequency of Natural Cross Pollination in a Mutant Strain of Soybean", *Current Science*, Vol. 41, No. 25, p. 832–833, 833(1972):

"Hybrid soybeans can also become a possibility if a technique is developed to sort out hybrid seeds from selfed seeds."

As indicated in "Bee Pollination of Soybeans" by Eric H. Erickson, *Proceedings of the Sixth Soybean Seed Research Conference* 1976, p. 46–49, 49:

"If hybrid soybeans become a reality, plant breeders must pay strict attention to floral characteristics and include compatibility of these factors in their breeding programs."

As indicated in "Cytogenetics in Soybean Improvement" by Reid R. Palmer, *Proceedings of Sixth Soybean Seed Research Conference* 1976, p. 56–66, 60:

"The announcement in 1974 (Bradner) of a patent on hybrid soybean seed production initially created some excitement. We should consider the possibility of hybrid soybeans. There are three major requirements for hybrid soybean production: (1) a male sterile, female fertile mutant(s) (either genetic or cytoplasmic-genetic); (2) a high level of pollen transfer from male fertile to male sterile (female parent) plants; and (3) sufficient hybrid vigor to warrant production. With the present genetic male steriles ($ms_1$ and $ms_2$), only 50% of the plants in a female production row will be male sterile. This is the highest percentage of male sterile plants that can be expected."

Finally, it is written by Charles A. Brim in "Implications of Male-Sterility in Soybeans", *Proceedings of the Sixth Soybean Seed Research Conference* 1976, p. 67–74, 67:

"The successful utilization of sterility mechanisms in producing commercial hybrids of mostly cross-pollinated crops such as corn, sorghum, and onions is well known. In these crops cytoplasmic male sterility coupled with nuclear genes which restore fertility has contributed greatly to decreased cost of seed production. Although not essential to seed production in corn, the sterility mechanism was adopted universally as a means of reducing costs. The success of hybrid corn, sorghum, and onions has not gone unnoticed by plant breeders working with other crops, and considerable effort has been expended in attempts to exploit hybrid vigor in almost every species of economic importance.

Soybeans are an obligate self-fertilizer and pollination takes place before the female parts of the flower are exposed to vectors which carry foreign pollen. Therefore, there is no alternative to a male sterility mechanism in achieving natural crossing in the species. But if we are concerned with hybrid seed production only, the availability of a sterility mechanism is of little use unless hybrid vigor is great enough to offset cost of production. The known male sterility mechanism in soybeans is determined by male-sterile plants can only be obtained from a "maintainer" line which segregates for fertility and sterility. The male fertile plants must be removed at flowering to obtain only cross seed."

As indicated, soybean plants (i.e., *Glycine max* plants) are recognized to be naturally self-pollinated plants which while being capable of undergoing cross-pollination rarely do so. Insects are reported by some researchers to carry pollen from one soybean plant to another and it generally is estimated that less than one percent of soybean seed formed in an open planting can be traced to cross-pollination, i.e., less than 1 percent of the soybean seed formed in an open planting is capable of producing $F_1$ hybrid soybean plants (i.e., hybrid soybean plants of the first filial generation). See the articles by Elbert R. Jaycox entitled "Ecological Relationships between Honey Bees and Soybeans" appearing in the *American Bee Journal*, Vol. 110(8): 306–307 (August 1970), Vol. 110(9): 343–345 (September 1970) and Vol. 110(10): 383–385, (October 1970).

The relatively low proportion of cross-pollination commonly observed in soybean plants when grown in nature can be traced to the characteristic floral configuration exhibited by soybean plants. The pistillate (female) and staminate (male) elements of soybean flowers are normally present on the same plant and are located within perfect flowers which contain both elements in a juxtaposed relationship. The opening of the individual soybean flowers (florets) is believed to be triggered by the temperature and the length of time the plant is exposed to light. However, the anthers and stigma continue to be tightly enclosed within petals (i.e., the portion of the flower known as the keel petals). When dihiscence of anther tissue occurs and pollen is shed from the anthers, it tends immediately to contact the stigma in the same floret and is retained there by the keel petals. A seed pod ultimately is formed from this fertilization assuming that the pollen does not abort. Accordingly, soybean plants normally are cleistogamous since the flowers are self-fertilized while still in the unopened state.

Cytoplasmic male sterility has never been observed in soybean plants in the past in spite of extensive plant breeding and prolonged searching within huge populations of soybean plants of many different varieties. However, some researchers have reported the existence of partial or complete male sterility in soybean plants which can be attributed to other factors such as chromosome abnormalities, viral conditions, genetic transmission attributable solely to nuclear genes, etc. None of the above types of male sterility heretofore observed has provided a real basis for the production of hybrid soybeans on a commercial scale. For instance, if the male sterility is attributable to nuclear genes the sterility can be perpetuated only through a line which segreates as for fertility and sterility. Accordingly, male fertile soybean plants are inevitably produced along with the male sterile soybean plants in the total absence of a meaningful control whereby only male sterile soybean plants are formed.

Representative publications which discuss the existence of some degree of sterility in soybean plants which is not attributable to the cytoplasm are as follows:

(1) "A Partially Male Sterile Strain of Soybeans", by C. E. Caviness, H. J. Walters, and D. L. Johnson, *Crop Science*, Vol. 10, p. 107–108, (Jan.–Feb. 1970), (2) "Inheritance of a Male-Sterile Character in Soybeans", C. A. Brim and M. F. Young, *Crop Science*, Vol. 11, p. 564–566, (July–Aug. 1971), (3) "Influence of Temperature on a Partially Male-Sterile Soybean Strain", by C. E. Caviness and B. L. Fagala, *Crop Science*, Vol. 13, p. 503–504 (Sept.–Oct. 1973), (4) "Implications of Male-Sterility in Soybeans", by A. Brim, *Proceedings of the Sixth Soybean Seed Research Conference* 1976, p. 67–71, (5) "Technology of Hybrid Soybeans", by W. H. Davis, *Proceedings of the Sixth Soybean Seed Research Conference* 1976, p. 72–74, (6) "A New Male-Sterile Strain in Wabash Soybeans", by H. K. Chaudhari and W. H. Davis, *J. of Heredity*, Vol. 68, p. 266–267 (1977), (7) "Pollen Production in Soybeans With Respect to Genotype, Environment, and Stamen Position", by R. G. Palmer, M. C. Albertson, and H. Heer, *Euphytica*, Vol. 27, p. 427–433 (1978), (8) "Genetics and Cytology of the $ms_3$ Male-Sterile Soybean", by R. G. Palmer, C. W. Johns, and P. S. Muir, *J. of Heredity*, Vol. 71, p. 343–348 (1980), (9) "Pollination of Male-Sterile Soybeans in Caged Plots", by P. D. Koelling, W. J. Kenworthy, and D. M. Caron, *Crop Science*, Vol. 21, p. 559–561 (July–Aug. 1981),

(10) "Variable Development in Anthers of Partially Male-Sterile Soybeans", by D. M. Stelly and R. G. Palmer, *J. of Heredity*, Vol. 73, p. 101–108 (1982), and

(11) "Genetics and Cytology of the $ms_4$ Male-Sterile Soybean", by X. Delanney and R. G. Palmer, *J. of Heredity*, Vol. 73, p. 219–223 (1982).

Unpublished data (to be published in a monograph in the future) recently provided by Reid G. Palmer indicates that the following genes were known in the past to cause sterility in soybeans:

| Gene Identification | Phenotype | Source Strain |
| --- | --- | --- |
| st2 | Asynaptic sterile | T241 |
| st3 | Asynaptic sterile | T242 |
| st4 | Desynaptic sterile | T258 |
| st5 | Desynaptic sterile | T272 |
| fs1 | Structural sterile | T269 |
| fs2 | Structural sterile | T269 |
| ft | Structural sterile | Gamma ray induced mutant |
| msp | Partial male sterile | T271 |
| ms1 | Male sterile | T260, T266, T267, T268 |
| ms2 | Male sterile | T259 |
| ms3 | Male sterile | T273 |
| ms4 | Male sterile | T274 |
| ms5 | Male sterile | T277 |

U.S. Pat. Nos. 3,903,645 and 4,077,157 to N. R. Bradner concern still different approaches to the production of hybrid soybeans In the former patent the hybrid seed is formed on a seed parent having an atypical exposed floral stigma. In each instance, the pollination is not fully controlled with both cross-pollination and self-pollination taking place. The resulting seeds are subsequently separated on the basis of size. The processes of these patents are yet to become a commercial reality.

It is an object of the present invention to provide an improved procedure for forming $F_1$ hybrid soybean plants which is capable of being readily implemented on a commercial scale.

It is an object of the present invention to provide an improved procedure for forming $F_1$ hybrid soybean plants wherein the requisite cross-pollination needed to produce the hybrid is precisely controlled thereby eliminating the possibility of unwanted self-pollination.

It is an object of the present invention to provide an improved procedure for forming $F_1$ hybrid soybean plants wherein the seed parent is the result of a controlled plant breeding program wherein previously widely dispersed factors are combined which have been found to be necessary if the requisite male sterility is to be exhibited.

It is an object of the present invention to provide an improved procedure for forming $F_1$ hybrid soybean plants wherein the seed parent is the result of a controlled plant breeding program wherein factors found necessary to express complete sterility are combined using well known techniques and readily available commercial soybean varieties.

It is an object of the present invention to provide soybean plants and seeds capable of forming the same which are fully male sterile as a result of the requisite combination of cytoplasmic and genetic factors found to be necessary to express this important characteristic.

It is a further object of the present invention to provide vigorous $F_1$ hybrid soybean plants wherein said vigor is attributable to heterosis and seeds capable of forming the same which are derived from a fully male sterile seed parent having the requisite combination of cytoplasmic and genetic factors found to be necessary to express this important characteristic.

It is an additional object of the present invention to provide novel agronomic technology which will increase soybean yields via heterosis and the income of farmers who choose to apply such technology.

These and other objects of the claimed invention, as well as its scope, nature, and utilization will be apparent to those skilled in plant technology from the following detailed description and appended claims.

SUMMARY OF THE INVENTION

It has been found that a process for the efficient production of seeds capable of growing male fertile $F_1$ hybrid *Glycine max* plants comprises:

(a) growing a substantially uniform population of male sterile soybean plants wherein the male sterility is attributable to the combination of an atypical Cms cytoplasm and two distinct pairs of recessive genes $r_1r_1$ and $r_2r_2$ in pollinating proximity to a substantially uniform population of male fertile soybean plants which possess at least one pair of dominant genes selected from the group consisting of $R_1R_1$ and $R_2R_2$ and which when crossed with the male sterile soybean plants enable the formation of seeds on the male sterile soybean plants which are capable of growing male fertile $F_1$ hydrid soybean plants, (b) crossing the male sterile soybean plants and the male fertile soybean plants (preferably with the aid of pollen carrying insects) whereby seeds are formed on said male sterile soybean plants, and (c) selectively recovering seeds which have formed on the male sterile soybean plants.

It has been found that a process for the efficient production of a substantially uniform binary seed blend containing a substantial proportion of seeds capable of growing male fertile $F_1$ hybrid *Glycine max* plants comprises:

(a) growing in a planting area a substantially random population of (i) male sterile soybean plants wherein the male sterility is attributable to the combination of an atypical Cms cytoplasm and two distinct pairs of recessive genes $r_1r_1$ and $r_2r_2$, and (ii) male fertile soybean plants which possess at least one pair of dominant genes selected from the group consisting of $R_1R_1$ and $R_2R_2$ and which when crossed with the male sterile soybean plants enable the formation of seeds on the male sterile soybean plants which are capable of growing male fertile $F_1$ hybrid soybean plants, (b) pollinating the substantially random population of soybean plants (preferably with the aid of pollen carrying insects) whereby seeds are formed on the male sterile plants which are capable of growing male fertile $F_1$ hybrid soybean plants and seeds are formed on the male fertile soybean plants as a result of self-pollination, and (c) recovering seeds which have formed on the substantially random population of soybean plants growing in the planting area.

It has been found that a process for maintaining male sterile *Glycine max* plants useful in the production of male fertile $F_1$ hybrid soybean plants comprises:

(a) growing a substantially uniform population of male sterile soybean plants wherein the male sterility is attributable to the combination of an atypical Cms cytoplasm and two distinct pairs of recessive genes $r_1r_1$ and $r_2r_2$ in pollinating proximity to a substantially uniform population of male fertile soybean plants which possess an N cytoplasm and two distinct pairs of recessive genes $r_1r_1$ and $r_2r_2$, (b) crossing the male sterile soybean plants and the male fertile soybean plants (preferably with the aid of pollen carrying insects) whereby seeds are formed on the male sterile soybean plants which upon growth yield additional male sterile soybean plants, and (c) selectively recovering seeds which have formed on the substantially uniform population of male sterile soybean plants.

A *Glycine max* seed product is provided consisting of a substantially homogeneous assemblage of seeds which upon growth yield male sterile soybean plants wherein the male sterility is attributable to the combination of an atypical Cms cytoplasm and two distinct pairs of recessive genes $r_1r_1$ and $r_2r_2$.

A *Glycine max* seed product is provided consisting of a substantially homogeneous assemblage of seeds which upon growth yield male fertile $F_1$ hybrid soybean plants which was the result of a cross-pollination between (a) a male sterile female parent wherein the male sterility was attributable to the combination of an atypical Cms cytoplasm and two pairs of recessive genes $r_1r_1$ and $r_2r_2$, and (b) a male fertile parent which possessed at least one pair of dominant genes selected from the group consisting of $R_1R_1$ and $R_2R_2$ which was capable of restoring male fertility to the progeny.

A *Glycine max* seed product is provided consisting of a substantially homogeneous binary admixture of seeds which upon growth yield:

(1) male fertile $F_1$ hybrid soybean plants which were the result of cross-pollination between:

(a) a male sterile female parent wherein the male sterility was attributable to the combination of an atypical Cms cytoplasm and two pairs of recessive genes $r_1r_1$ and $r_2r_2$, and (b) a male fertile male parent which possessed at least one pair of dominant genes selected from the group consisting of $R_1R_1$ and $R_2R_2$ which was capable of restoring male fertility to the off-spring, and (2) male fertile soybean plants which were the result of the self-pollination of the male fertile male parent (b) identified with respect to binary component (1).

Plants of *Glycine max* are provided which exhibit male sterility which is attributable to the combination of an atypical Cms cytoplasm and two distinct pairs of recessive genes $r_1r_1$ and $r_2r_2$.

Male fertile $F_1$ hybrid plants of *Glycine max* are provided which are the result of a cross-pollination between (a) a male sterile female parent wherein the male sterility was attributable to the combination of an atypical Cms cytoplasm and two pairs of recessive genes $r_1r_1$ and $r_2r_2$, and (b) a male fertile male parent which possessed at least one pair of dominant genes selected from the group consisting of $R_1R_1$ and $R_2R_2$ which was capable of restoring male fertility to the progeny.

A substantially uniform binary stand of *Glycine max* plants of at least one acre is provided consisting of:

(1) male fertile $F_1$ hybrid soybean plants which were the result of cross-pollination between:

(a) a male sterile female parent wherein the male sterility was attributable to the combination of an atypical Cms cytoplasm and two pairs of recessive genes $r_1r_1$ and $r_2r_2$, and (b) a male fertile male parent which possessed at least one pair of dominant genes selected from the group consisting of $R_1R_1$ and $R_2R_2$ which was capable of restoring male fertility to the off-spring, and (2) male fertile soybean plants which were the result of the self-pollination of the male fertile parent (b) identified with respect to the binary component (1).

DESCRIPTION OF THE PREFERRED EMBODIMENTS

It now has been demonstrated that three factors found to exist in available sources of *Glycine max* plants when properly combined in a single plant by the intervention of man provide a means to accomplish hybrid soybean production on a highly efficient basis. Such factors (as described hereafter) have heretofore existed separately while dispersed in soybean plants from widely differing sources, and are believed to have never been heretofore combined in the required manner in a single plant. Also, even if a plant which possesses the required combination of essential factors is placed in the field and is grown without the continuing intervention of man it will not perpetuate itself, and will be promptly lost for all practical purposes.

The male sterile soybean plants which are required are fully female fertile but produce no viable pollen thereby precluding the possibility of unwanted self-pollination. These plants accordingly can satisfactorily serve as the female or seed parent using the hybridization procedures described hereafter. Accordingly, all of the seed formed on the male sterile soybean plants following pollination will be capable of forming the desired $F_1$ hybrid plants.

In accordance with the concept of the present invention, it has been found essential that the female fertile male sterile soybean plants possess (1) a Cms cytoplasm, (2) a distinct pair of recessive $r_1r_1$ genes in the cell nucleus, and (3) a distinct pair of recessive $r_2r_2$ genes in the cell nucleus, which in combination render the plant incapable of producing viable pollen while otherwise carrying out the usual plant functions required to produce soybeans if viable pollen is provided from another soybean plant. As heretofore indicated, prior to the work of the present inventor, cytoplasmicly controlled male sterility of any type had not been available in soybean plants in spite of extensive research efforts.

It has been previously recognized by crop scientists that *Glycine max* plants are annuals which cannot be satisfactorily propagated by asexual means since if new plants are formed by cuttings, the new plants are of a progressively smaller size. However, the female fertile male sterile soybean plants of the present invention can be successfully propagated by sexual means as described hereafter. Also, these male sterile plants unlike soybean plants which rely exclusively on nuclear genes for sterility can be conveniently perpetuated or maintained without unwanted segregation with respect to sterility, as described hereafter.

The atypical Cms cytoplasm of the female fertile male sterile soybean plants can be derived through the female parent from an appropriate cytoplasmic source. For instance, it has been found that the requisite Cms cytoplasm required in the female fertile fully male sterile soybean plants can be conveniently derived from a Mandarin cytoplasmic source through the female parent. Many Northern soybean varieties are derived from this cytoplasmic source. Plants of this origin have been found inherently to possess an atypical cytoplasm of the type required to practice the present invention. Since this required factor is not contributed by nuclear genes and is not transmitted through the pollen, it can be considered cytoplasmic, non-Mendelian, extrachromosomal, uniparental, and maternal. Representative commercially available soybean plants which are derived maternally from a Mandarin cytoplasmic source are Adelphia, Chippewa, Chippewa 64, Clark, Classic I, Classic II, Columbus, Cutler, Disoy, Elf, Ford, Grant, Harosoy, Harosoy 63, Hobbitt, Kent, Lincoln, Lindarin, Lindarin 63, Magna, Prize, Provar, Rampage, RA 203, RA 402, RA 481, RAX 56, RAX 57, RAX 61, RAX 62, RAX 66, SB 27, Shelby, Traverse, Wayne, Wirth, Williams, etc. A particularly good source for the required Cms cytoplasm has been found to be the Elf variety which was introduced during 1977 by AR-SEA-USDA, the Ohio Agric. Res. and Dev. Center, and the U. of Illinois Agric. Res. Station. In 1981 this variety was registered by the Crop Sci. Soc. of Am. as Reg. No. 150.

It should be emphasized that when plants of the above-identified varieties are inspected for the possible absence of viable pollen production, that male sterile plants (either partially male sterile or completely male sterile) wherein the sterility is attributable to the cytoplasm are not observed. It has been found that such sterility is not expressed even though the required atypical Cms cytoplasm is present because it is not in combination with the required recessive genes discussed hereafter. Instead such varieties can be shown to possess at least one pair of dominant $R_1R_1$ or $R_2R_2$ genes (usually both pairs) which always leads to the expression of the usual viable pollen production even in the presence of the Cms cytoplasm.

The pair of recessive genes $r_1r_1$ for male sterility present in the female fertile fully male sterile plants employed in the present invention can be derived through its male parent from a first gene source which possesses such genes. Unlike the male sterile plants, the first gene source possesses a usual N cytoplasm which can be termed a "normal" or "neutral" cytoplasm. When such cytoplasm is present, cytoplasmicly controlled male sterility is not exhibited regardless of the nuclear genes which are present.

It has been found that the requisite pair of $r_1r_1$ recessive genes in the cell nucleus of the female fertile fully male sterile soybean plants conveniently can be derived through the male parent from a Dunfield germplasm base. Many Southern soybean varieties are derived from this germplasm base. Plants of this origin have been found inherently to possess the required pair of recessive genes which has been designated $r_1r_1$. Representative commercially available soybean plants from which the $r_1r_1$ recessive genes may be derived are Bedford, Bethel, Centennial, Dare, Dyer, Forrest, Hill, Kirby, RA(d)41, RA 581, RA 603, RA 605, RA 606, RA 680, Tracy, Wabash, York, etc. A particularly good source for the required $r_1r_1$ recessive genes has been found to be the Bedford variety which was introduced during 1978 by FR-SEA-USDA, and the Tennessee and Mississippi Agric. Expt. Stations. This variety was registered by the Crop Sci. Soc. of Am. as Reg. No. 118.

It further should be emphasized that when plants of the above-identified varieties having $r_1r_1$ genes are inspected for the possible absence of viable pollen production, that male sterile plants (either partially male sterile or completely male sterile) wherein the sterility is attributable to the cytoplasm are not observed. It has been found that such sterility will not be expressed unless the atypical Cms cytoplasm is present along with recessive genes $r_2r_2$. Instead such varieties can be shown to possess dominant $R_2R_2$ genes which restore male fertility and an N cytoplasm.

The pair of recessive genes $r_2r_2$ for male sterility present in the female fertile fully male sterile plants employed in the present invention can be derived through its male parent from a second gene source which possesses such genes. Such $r_2r_2$ genes are present as a distinct gene pair apart from the $r_1r_1$ genes in the female fertile fully male sterile plants (i.e., they are present at different loci). Unlike the male sterile plants, the second gene source possesses a usual N cytoplasm which can be termed a "normal" or "neutral" cytoplasm. As previously indicated, when such cytoplasm is present cytoplasmicly controlled male sterility is not exhibited regardless of the nuclear genes which are present.

It has been found that the requisite pair of $r_2r_2$. recessive genes in the cell nucleus of the female fertile fully male sterile soybean plants conveniently can be derived through the male parent from a Tokyo germplasm base. Many Southern soybean varieties are derived from this germplasm base. Plants of this origin have been found inherently to possess the required pair of recessive genes which has been designated $r_2r_2$. Representative commercially available soybean plants from which the $r_2r_2$ recessive genes may be derived are Bragg, Braxton, Cobb, Govan, Hardee, Hutton, Jackson, Kirby, Majos, Ogden, RA 604, RA 701, RA 800, Volstate, Wright, etc. A particularly good source for the required $r_2r_2$ recessive genes has been found in the Braxton variety which was introduced during 1979 by the USDA and various state Agric. Expt. Stations.

It additionally should be emphasized that when plants of the above-identified varieties having $r_2r_2$ genes are inspected for the possible absence of viable pollen production, that male sterile plants (either partially male sterile or completely male sterile) wherein the sterility is attributable to the cytoplasm are not observed. It has been found that such sterility will not be expressed unless the atypical Cms cytoplasm is present along with recessive genes $r_1r_1$. Instead such varieties can be shown to possess dominant $R_1R_1$ genes which restore male fertility and an N cytoplasm.

The female fertile fully male sterile plants employed in the present invention can be maintained or perpetuated in spite of the male sterility by crossing with pollen from a soybean plant which possesses an N cytoplasm and the two distinct pairs of recessive genes $r_1r_1$ and $r_2r_2$. Such maintainer plants are formed by the intervention of man through the combination of the required factors and are not found in nature. The progeny of this cross will again be female fertile and fully male sterile. Also, should the female fertile fully male sterile plants employed in the present invention be crossed with pollen from a male fertility restorer (i.e. having dominant $R_1R_1$ genes and/or dominant $R_2R_2$ genes), then the progeny will be fully fertile $F_1$ hybrid soybean plants. Suitable male fertility restorer plants are readily available without modification. For instance, any of the varieties heretofore named can perform this function. The only requirement is that plants which supply the pollen possess at least one pair of the required dominant fertility restoring genes.

The development of female fertile fully male sterile soybean plants for use in the present invention, as well as maintainer plants for the same, can be exemplified through a plant breeding program employing plants of the Elf, Bedford, and Braxton varieties. It should be understood, however, that the presently claimed invention can be equally well practiced through the utilization of soybean plants of other varieties provided the essential criteria set forth herein nevertheless are met. Initially plants of the Bedford variety (i.e., having an $r_1r_1$ gene source) are crossed by hand with pollen from plants of the Braxton variety (i.e., having an $r_2r_2$ gene source) wherein each of these two plant sources exhibits the usual N cytoplasm commonly observed in Southern soybean plants. The progeny of this cross are fully female fertile and male fertile and serve as a pollen source for plants of the Elf variety (i.e., having a Cms cytoplasmic source). Such crossing to the Elf variety is again carried out by hand under controlled conditions in the absence of Elf self-pollination. When the $F_1$ seed which has formed on the Elf female parent is grown, it will be noted that all of the resulting plants are fully female fertile and male fertile. Each of these $F_1$ plants is next self-pollinated through succeeding generations to form $F_2$, $F_3$, and $F_4$ controlled populations which are inspected for the absence of viable pollen It is observed that some plants are female fertile fully male fertile, some plants are female fertile partially male fertile (i.e., produce only a limited quantity of viable pollen), and some plants are female fertile fully male sterile (i.e., produce no viable pollen).

The fact that none of the $F_1$ plants were male sterile confirms that the sterility subsequently observed was not controlled solely by nuclear genes. The ratios in which the plants segregate in the $F_2$, $F_3$ and $F_4$ generations with respect to male sterility confirm that the sterility is the result of a more complex cytoplasmic/genetic system in which the genetic aspect is bifactorial (i.e., two distinct gene pairs at different loci are operative and are interacting with the cytoplasm). The fully male sterile plants possess the Cms cytoplasm and the $r_1r_1$ and $r_2r_2$ genes. The partially male sterile plants possess the Cms cytoplasm and (1) $R_1r_1$ and $r_2r_2$ genes or (2) $r_1r_1$ and $R_2r_2$ genes. The fully male fertile plants possess the Cms cytoplasm and $R_1R_1$ genes and/or $R_2R_2$ genes. When the fully male sterile plants are crossed with pollen from the Elf, Bedford, and Braxton varieties, all $F_1$ progeny are fully male fertile. Accordingly, this indicates that no single parent variety (e.g. Elf, Bedford, or Braxton) possesses sufficient genes to create male sterile $F_1$ plants.

Once the required male sterile plants are on hand, suitable maintainer plants (i.e. those having an N cytoplasm in combination with $r_1r_1$ and $r_2r_2$ genes) can be developed by standard plant breeding techniques involving intercrossing and introgression. For instance, the required $r_1r_1$ and $r_2r_2$ genes can be provided in existing soybean varieties of agronomic importance having the usual N cytoplasm by intercrossing and possible backcrossing by hand with the pollen derived from female fertile partially male fertile plants obtained from the $F_2$, $F_3$ and $F_4$ controlled populations obtained during or subsequent to the development of the male sterile plants (described above). The $F_1$ plants from this cross are grown and are self-pollinated to form $F_2$ plants. Test crosses of the fully male sterile plants previously developed with pollen derived from the $F_2$ plants are made and those plants are identified and preserved which are capable of yielding fully male sterile $F_1$ progeny. Such plants possess the full complement of recessive $r_1r_1$ and $r_2r_2$ genes. Once identified such homozygous maintainer plants can be perpetuated by self-pollination.

When producing seeds capable of growing male fertile $F_1$ hybrid soybean plants in accordance with one embodiment of the process of the present invention, the required male sterile soybean plants (previously described) are grown as a substantially uniform population in pollinating proximity to a substantially uniform population of soybean plants having the required dominant restorer genes (previously described). In the context of the present invention "pollinating proximity" specifies that the two types of parent plants are sufficiently near that pollen can be transferred without loss of its viability. The restorer plants conveniently can be a pure line variety. For instance, the two types of plants can be grown adjacent to each other as alternating strips. In a preferred embodiment approximately 2, 4, or 6 rows of the required male sterile soybean plants form a substantially uniform population and alternate with a substantially uniform population of approximately two rows of the plants which restore fertility in the $F_1$ progeny. Following pollen transfer from the restorer plants to the required male sterile plants, seeds are formed on the male sterile soybean plants. The restorer soybean plants commonly are self-pollinated and seeds also form on them. At harvest time the seeds are selectively recovered from each of the substantially uniform plant populations. Accordingly, the seeds which are recovered from the male sterile soybean plants are a substantially homogeneous assemblage of seeds which upon growth yield male fertile $F_1$ hybrid soybean plants. Such seeds preferably are sufficient to form a substantially uniform stand of the $F_1$ hybrid soybean plants of at least one acre.

In accordance with another embodiment of the process of the present invention, a substantially uniform binary seed blend is formed containing a substantial proportion (e.g. at least one-half by number) of seeds capable of growing male fertile $F_1$ hybrid soybean plants. Such blend can be formed by growing in a planting area a substantially random population of the required male sterile soybean plants (previously described) together with plants having the required dominant restorer genes (previously described). For instance, approximately 80 to 95 percent (e.g. approximately 90 percent) of the plants in the random population can be the required male sterile plants and approximately 5 to 20 percent (e.g. approximately 10 percent) of the plants in the random population can possess the dominant restorer genes. Following pollen transfer the seeds formed on the male sterile soybean plants are capable of forming the male fertile $F_1$ hybrid soybean plants, and the seeds formed on the restorer soybean plants are the result of self-pollination. The resulting seeds formed on the substantially random population of soybean plants next is harvested in bulk and can be planted in bulk by the grower.

The level of cross-pollination occurring in the random population of plants can be visually observed by inspecting the resulting seeds or the plants produced when the resulting seeds are grown if one incorporates an appropriate genetic marker system into the parent plants which gives one appearance upon cross-pollination and another appearance upon self-pollination. The genetic marker can take the form of a recessive gene which expresses itself upon self-pollination, but which is dominated by another gene giving a different appearance when cross-pollination takes place. Under such circumstances the restorer plants could be homozygous recessive for such trait and the male sterile plants homozygous dominant for such trait. For instance, the genetic marker can be a distinctive pubescence color (e.g. gray pubescence vs. tawny pubescence), flower color (e.g. white flowers vs. purple flowers), seed pod color (e.g. tan vs. brown pods), hilum appearance (e.g. yellow vs. black hilum or buff vs. black hilum), etc.

Alternatively, the required male sterile soybean plants (previously described) can be maintained, perpetuated, and multiplied by planting a substantially uniform population of the same in pollinating proximity to a substantially uniform population of the required maintainer plants (previously described). For instance, the two types of plants can be grown adjacent to each other as alternating strips as described earlier with respect to the production of male fertile $F_1$ hybrid seed. Following pollen transfer from the maintainer plants to the male sterile plants seeds are formed on the male sterile soybean plants. The maintainer plants are self-pollinated and seeds also form on them. At harvest time the seeds are selectively harvested from each of the substantially uniform plant populations. Accordingly, the seeds which are recovered from the male sterile soybean plants is a substantially homogeneous assemblage of seeds which upon growth yield male sterile soybean plants wherein the male sterility is attributable to the combination of an atypical Cms cytoplasm and two distinct pairs of recessive genes $r_1r_1$ and $r_2r_2$. When planted such seeds preferably are capable of forming a substantially uniform stand of at least 1000 of the required male sterile plants. The seeds which are selectively recovered from the maintainer plants can be planted to produce additional maintainer plants or sold as a commercial soybean product.

As previously indicated, the cross-pollination required in the process steps of the present invention can be satisfactorily carried out with the aid of pollen carrying insects. In a particularly preferred embodiment crossing or pollination is carried out with the aid of pollen carrying bees. Representative pollen carrying insects for use in the process include honey bees, bumble bees, leafcutter bees, solitary bees, etc. Such insects can be relied upon to randomly visit the plant blossoms in search of pollen and/or nectar. The leafcutter bees can be used to advantage in Northern climates. Alternatively, the crossing or pollination can be carried out with the aid of the wind provided pollen parent soybean plants are selected having a flower morphology which adequately exposes the pollen to the wind and the seed parent soybean plants have a sufficiently exposed floral morphology to receive such pollen. As a further alternative, the required crossing or pollination can be carried out with the aid of mechanized or hand pollen transfer.

In order to enhance the incidence of insect visitation and the pollen transfer required to accomplish a high level of cross-pollination several measures optionally can be utilized. For instance, the male sterile plants can be selected for large blossom size to aid insect entry and/or for a showy appearance, the presence of an attractive odor, and an abundance of attractive pollen and nectar. Also in a preferred embodiment, the required male sterile seed parent plants will bloom either simultaneously with or slightly later (e.g. 2 to 5 days later) than the pollen parent plants. Additionally, the soybean plants can be grown under a controlled irrigation system whereby excess water is applied to induce vegetative growth followed by flower formation. The water subsequently can be withheld to induce nectar flow which proves to be particularly attractive to insects.

The concept of the present invention provides the soybean grower an opportunity to produce and harvest soybeans in increased yields which are attributable to heterosis or hybrid vigor made possible by the precise control of the cross-pollination described herein.

Although the invention has been described with preferred embodiments, it is to be understood that variations and modifications may be resorted to as will be apparent to those skilled in the art. Such variations and modifications are to be considered within the purview and scope of the claims appended hereto.

I claim:

1. A process for the efficient production of seeds capable of growing male fertile $F_1$ hybrid *Glycine max* plants comprising:
   (a) growing a substantially uniform population of male sterile soybean plants wherein said male sterility is attributable to the combination of an atypical Cms cytoplasm and two distinct pairs of recessive genes $r_1r_1$ and $r_2r_2$ in pollinating proximity to a substantially uniform population of male fertile soybean plants which possess at least one pair of dominant genes selected from the group consisting of $R_1R_1$ and $R_2R_2$ and which when crossed with said male sterile soybean plants enable the formation of seeds on said male sterile soybean plants which are capable of growing male fertile $F_1$ hybrid soybean plants,
   (b) crossing said male sterile soybean plants and said male fertile soybean plants whereby seeds are formed on said male sterile soybean plants, and
   (c) selectively recovering the seeds which have formed on said male sterile soybean plants.

2. A process for the efficient production of seeds capable of growing male fertile $F_1$ hybrid *Glycine max* plants according to claim 1 wherein with respect to said male sterile soybean plants said atypical Cms cytoplasm was derived through its female parent from an appropriate cytoplasmic source, and in which said recessive genes $r_1r_1$ were derived through its male parent from a first gene source which possessed an N cytoplasm and said $r_1r_1$ genes, and in which said recessive genes $r_2r_2$ additionally were derived through its male parent from a second gene source which possessed an N cytoplasm and said $r_2r_2$ genes.

3. A process for the efficient production of seeds capable of growing male fertile $F_1$ hybrid *Glycine max* plants according to claim 1 wherein with respect to said male sterile soybean plants said atypical Cms cytoplasm was derived through its female parent from a Mandarin cytoplasmic source, and in which said recessive genes $r_1r_1$ were derived through its male parent from a Dunfield germplasm base having an N cytoplasm and in which said recessive genes $r_2r_2$ additionally were derived through its male parent from a Tokyo germplasm base having an N cytoplasm.

4. A process for the efficient production of seeds capable of growing male fertile $F_1$ hybrid *Glycine max* plants according to claim 3 wherein with respect to said male sterile soybean plants said atypical Cms cytoplasm was derived through its female parent from the Elf variety, and in which said recessive genes $r_1r_1$ were derived through its male parent from the Bedford variety, and in which said recessive genes $r_2r_2$ additionally were derived through its male parent from the Braxton variety.

5. A process for the efficent production of seeds capable of growing male fertile $F_1$ hybrid *Glycine max* plants according to claim 1 wherein said substantially uniform populations of male sterile soybean plants and male fertile soybean plants are grown in alternating strips.

6. A process for the efficent production of seeds capable of growing male fertile $F_1$ hybrid *Glycine max* plants according to claim 1 which includes the additional step of selectively recovering seeds formed on said substantially uniform population of male fertile soybean plants grown in step (a).

7. A process for the efficient production of seeds capable of growing male fertile $F_1$ hybrid *Glycine max* plants according to claim 1 wherein said male fertile soybean plants grown in step (a) are a pure line variety.

8. A process for the efficient production of seeds capable of growing male fertile $F_1$ hybrid *Glycine max* plants according to claim 1 wherein said crossing of step (b) is carried out with the aid of pollen carrying insects.

9. A process for the efficient production of seeds capable of growing male fertile $F_1$ hybrid *Glycine max* plants comprising:
   (a) growing a substantially uniform population of male sterile soybean plants wherein said male sterility is attributable to the combination of an atypical Cms cytoplasm and two distinct pairs of recessive genes $r_1r_1$ and $r_2r_2$ in pollinating proximity to a substantially uniform population of male fertile soybean plants which possess at least one pair of dominant genes selected from the group consisting of $R_1R_1$ and $R_2R_2$ and which when crossed with said male sterile soybean plants enable the formation of seeds on said male sterile soybean plants which are capable of growing male fertile $F_1$ hybrid soybean plants,
   (b) crossing said male sterile soybean plants and said male fertile soybean plants with the aid of pollen carrying bees whereby seeds are formed on said male sterile soybean plants, and
   (c) selectively recovering the seeds which have formed on said male sterile soybean plants.

10. A process for the efficient production of a substantially uniform binary seed blend containing a substantial proportion of seeds capable of growing male fertile $F_1$ hybrid *Glycine max* plants comprising:
    (a) growing in a planting area a substantially random population of (i) male sterile soybean plants wherein said male sterility is attributable to the combination of an atypical Cms cytoplasm and two distinct pairs of recessive genes $r_1r_1$ and $r_2r_2$, and (ii) male fertile soybean plants which possess at least one pair of dominant genes selected from the group consisting of $R_1R_1$ and $R_2R_2$ and which when crossed with said male sterile soybean plants enable the formation of seeds on said male sterile soybean plants which are capable of growing male fertile $F_1$ hybrid soybean plants,
    (b) pollinating said substantially random population of soybean plants whereby seeds are formed on said male sterile plants which are capable of growing male fertile $F_1$ hybrid soybean plants and seeds are formed on said male fertile soybean plants as a result of self-pollination, and
    (c) recovering seeds which have formed on said substantially random population of soybean plants growing in said planting area.

11. A process for the efficient production of a substantially uniform binary seed blend containing a substantial proportion of seeds capable of growing male fertile $F_1$ hybrid *Glycine max* plants according to claim 10 wherein with respect to said male sterile soybean plants of said substantially random population said atypical Cms cytoplasm was derived through its female parent from an appropriate cytoplasmic source, and in which said recessive genes $r_1r_1$ were derived through its male parent from a first gene source which possessed an N cytoplasm and said $r_1r_1$ genes, and in which said recessive genes $r_2r_2$ additionally were derived through its male parent from a second gene source which possessed an N cytoplasm and said $r_2r_2$ genes.

12. A process for the efficient production of a substantially uniform binary seed blend containing a substantial proportion of seeds capable of growing male fertile $F_1$ hybrid *Glycine max* plants according to claim 10 wherein said atypical Cms cytoplasm was derived through its female parent from a Mandarin cytoplasmic source, and in which said recessive genes $r_1r_1$ were derived through its male parent from a Dunfield germplasm base having an N cytoplasm, and in which said recessive genes $r_2r_2$ additionally were derived through its male parent from a Tokyo germplasm base having an N cytoplasm.

13. A process for the efficient production of a substantially uniform binary seed blend containing a substantial proportion of seeds capable of growing male fertile $F_1$ hybrid *Glycine max* plants according to claim 12 wherein with respect to said male sterile soybean plants of said substantially random population said atypical Cms cytoplasm was derived through its female parent from the Elf variety, and in which said recessive genes $r_1r_1$ were derived through its male parent from the Bedford variety, and in which said recessive genes $r_2r_2$ additionally were derived through its male parent from the Braxton variety.

14. A process for the efficent production of a substantially uniform binary seed blend containing a substantial proportion of seeds capable of growing male fertile $F_1$ hybrid *Glycine max* plants according to claim 10 wherein said male fertile soybean plants of said substantially random population are a pure line variety.

15. A process for the efficient production of a substantially uniform binary seed blend containing a substantial proportion of seeds capable of growing male fertile $F_1$ hybrid *Glycine max* plants according to claim 10 wherein said pollinating of step (b) is carried out with the aid of pollen carrying insects.

16. A process for the efficient production of a substantially uniform binary seed blend containing a substantial proportion of seeds capable of growing male fertile $F_1$ hybrid *Glycine max* plants comprising:
    (a) growing in a planting area a substantially random population of (i) male sterile soybean plants wherein said male sterility is attributable to the combination of an atypical Cms cytoplasm and two distinct pairs of recessive genes $r_1r_1$ and $r_2r_2$, and (ii) male fertile soybean plants which possess at least one pair of dominant genes selected from the group consisting of $R_1R_1$ and $R_2R_2$ and which when crossed with said male sterile soybean plants enable the formation of seeds on said male sterile soybean plants which are capable of growing male fertile $F_1$ hybrid soybean plants,
    (b) pollinating said substantially random population of soybean plants with the aid of pollen carrying bees whereby seeds are formed on said male sterile plants which are capable of growing male fertile $F_1$ hybrid soybean plants and seeds are formed on said male fertile soybean plants as a result of self-pollination, and
    (c) recovering seeds which have formed on said substantially random population of soybean plants growing in said planting area.

17. A process for maintaining male sterile *Glycine max* plants useful in the production of male fertile $F_1$ hybrid soybean plants comprising:
    (a) growing a substantially uniform population of male sterile soybean plants wherein said male sterility is attributable to the combination of an atypical Cms cytoplasm and two distinct pairs of recessive genes $r_1r_1$ and $r_2r_2$ in pollinating proximity to a substantially uniform population of male fertile soybean plants which possess an N cytoplasm and two distinct pairs of recessive genes $r_1r_1$ and $r_2r_2$,
    (b) crossing said male sterile soybean plants and said male fertile soybean plants whereby seeds are formed on said male sterile soybean plants which upon growth yield additional male sterile soybean plants, and
    (c) selectively recovering seeds which have formed on said substantially uniform population of male sterile soybean plants.

18. A process for maintaining male sterile *Glycine max* plants useful in the production of male fertile $F_1$ hybrid soybean plants according to claim 17 wherein with respect to said male sterile soybean plants of said substantially uniform population of step (a) said atypical Cms cytoplasm was derived through its female parent from an appropriate cytoplasmic source, and in which said recessive genes $r_1r_1$ were derived through its male parent from a first gene source which possessed an N cytoplasm and said $r_1r_1$ genes, and in which said recessive genes $r_2r_2$ additionally were derived through its male parent from a second gene source which possessed an N cytoplasm and said $r_2r_2$ genes.

19. A process for maintaining male sterile *Glycine max* plants useful in the production of male fertile $F_1$ hybrid soybean plants according to claim 17 wherein with respect to said male sterile soybean plants of said substantially uniform population of step (a) said atypical Cms cytoplasm was derived through its female parent from a Mandarin cytoplasmic source, and in which said recessive genes $r_1r_1$ were derived through its male parent from a Dunfield germplasm base having an N cytoplasm, and in which said recessive genes $r_2r_2$ additionally were derived through its male parent from a Tokyo germplasm base having an N cytoplasm.

20. A process for maintaining male sterile *Glycine max* plants useful in the production of male fertile $F_1$ hybrid soybean plants according to claim 19 wherein with respect to said male sterile soybean plants of said substantially uniform population of step (a) said atypical Cms cytoplasm was derived through its female parent from the Elf variety, and in which said recessive genes $r_1r_1$ were derived through its male parent from the Bedford variety, and in which recessive genes $r_2r_2$ additionally were derived through its male parent from the Braxton variety.

21. A process for maintaining male sterile *Glycine max* plants useful in the production of male fertile $F_1$ hybrid soybean plants according to claim 17 wherein said crossing of step (b) is carried out with the aid of pollen carrying insects.

22. A process for maintaining male sterile *Glycine max* plants useful in the production of male fertile $F_1$ hybrid soybean plants comprising:
   (a) growing a substantially uniform population of male sterile soybean plants wherein said male sterility is attributable to the combination of an atypical Cms cytoplasm and two distinct pairs of recessive genes $r_1r_1$ and $r_2r_2$ in pollinating proximity to a substantially uniform population of male fertile soybean plants which possess an N cytoplasm and two distinct pairs of recessive genes $r_1r_1$ and $r_2r_2$,
   (b) crossing said male sterile soybean plants and said male fertile soybean plants with the aid of pollen carrying bees whereby seeds are formed on said male sterile soybean plants which upon growth yield additional male sterile soybean plants, and
   (c) selectively recovering seeds which have formed on said substantially uniform population of male sterile soybean plants.

23. A *Glycine max* seed product consisting of a substantially homogeneous assemblage of seeds which upon growth yield male sterile soybean plants wherein said male sterility is attributable to the combination of an atypical Cms cytoplasm and two distinct pairs of recessive genes $r_1r_1$ and $r_2r_2$.

24. A *Glycine max* seed product consisting of a substantially homogeneous assemblage of seeds which upon growth yield male sterile soybean plants according to claim 23, wherein said seed product was formed via a controlled plant breeding program in which said atypical Cms cytoplasm was derived through the female parent from an appropriate cytoplasmic source, and in which said recessive genes $r_1r_1$ were derived through the male parent from a first gene source which possessed an N cytoplasm and said $r_1r_1$ genes, and in which said recessive genes $r_2r_2$ additionally were derived through the male parent from a second gene source which possessed an N cytoplasm and said $r_2r_2$ genes.

25. A *Glycine max* seed product consisting of a substantially homogeneous assemblage of seeds which upon growth yield male sterile soybean plants according to claim 23, wherein said seed product was formed via a controlled plant breeding program in which said atypical Cms cytoplasm was derived through the female parent from a Mandarin cytoplasmic source, and in which said recessive genes $r_1r_1$ were derived through the male parent from a Dunfield germplasm base having an N cytoplasm, and in which said recessive genes $r_2r_2$ additionally were derived through the male parent from a Tokyo germplasm base having an N cytoplasm.

26. A *Glycine max* seed product consisting of a substantially homogeneous assemblage of seeds which upon growth yield male sterile soybean plants according to claim 25, wherein said seed product was formed via a controlled plant breeding program in which said atypical Cms cytoplasm was derived through the female parent from the Elf variety, and in which said recessive genes $r_1r_1$ were derived through the male parent from the Bedford variety, and in which said recessive genes $r_2r_2$ additionally were derived through the male parent from the Braxton variety.

27. A *Glycine max* seed product consisting of a substantially homogenous assemblage of seeds which upon growth yield male fertile $F_1$ hybrid soybean plants which was the result of a cross-pollination between (a) a male sterile female parent wherein the male sterility was attributable to the combination of an atypical Cms cytoplasm and two pairs of recessive genes $r_1r_1$ and $r_2r_2$, and (b) a male fertile parent which possessed at least one pair of dominant genes selected from the group consisting of $R_1R_1$ and $R_2R_2$ which was capable of restoring male fertility to the progeny.

28. A *Glycine max* seed product consisting of a substantially homogeneous assemblage of seeds which upon growth yield male fertile $F_1$ hybrid soybean plants according to claim 27 wherein said male sterile female parent (a) was formed via a controlled plant breeding program in which said atypical Cms cytoplasm was derived through its female parent from an appropriate cytoplasmic source, and in which said recessive genes $r_1r_1$ were derived through its male parent from a first gene source which possessed an N cytoplasm and said $r_1r_1$ genes, and in which said recessive genes $r_2r_2$ additionally were derived through its male parent from a second gene source which possessed an N cytoplasm and said $r_2r_2$ genes.

29. A *Glycine max* seed product consisting of a substantially homogeneous assemblage of seeds which upon growth yield male fertile $F_1$ hybrid soybean plants according to claim 27 wherein said male sterile female parent (a) was formed via a controlled plant breeding program in which said atypical Cms cytoplasm was derived through its female parent from a Mandarin cytoplasmic source, and in which said recessive genes $r_1r_1$ were derived through its male parent from a Dunfield germplasm base having an N cytoplasm, and in which said recessive genes $r_2r_2$ additionally were derived through its male parent from a Tokyo germplasm base having an N cytoplasm.

30. A *Glycine max* seed product consisting of a substantially homogeneous assemblage of seeds which upon growth yield male fertile $F_1$ hybrid soybean plants according to claim 29 wherein said male sterile female parent (a) was derived through its female parent from the Elf variety, and in which said recessive genes $r_1r_1$ were derived through its male parent form the Bedford variety, and in which said recessive genes $r_2r_2$ additionally are derived through its male parent from the Braxton variety.

31. A *Glycine max* seed product consisting of a substantially homogeneous binary admixture of seeds which upon growth yield:
   (1) male fertile $F_1$ hybrid soybean plants which were the result of cross-pollination between:
      (a) a male sterile female parent wherein the male sterility was attributable to the combination of an atypical Cms cytoplasm and two pairs of recessive genes $r_1r_1$ and $r_2r_2$, and
      (b) a male fertile male parent which possessed at least one pair of dominant genes selected from the group consisting of $R_1R_1$ and $R_2R_2$ which was capable of restoring male fertility to the offspring, and
   (2) male fertile soybean plants which were the result of the self-pollination of said male fertile male parent (b) identified with respect to binary component (1).

32. A *Glycine max* seed product consisting of a substantially homogeneous binary admixture of seeds according to claim 31 wherein the (a) parent of said binary component (1) was formed via a controlled plant breeding program in which said atypical Cms cytoplasm was derived through its female parent from an appropriate cytoplasmic source and in which said recessive genes $r_1r_1$ were derived through its male parent from a first gene source which possessed an N cytoplasm and said $r_1r_1$ genes, and in which said recessive genes $r_2r_2$ additionally were derived through its male parent from a second gene source which possessed an N cytoplasm and said $r_2r_2$ genes.

33. A *Glycine max* seed product consisting of a substantially homogeneous binary admixture of seeds according to claim 31 wherein the (a) parent of said binary component (1) was formed via a controlled plant breeding program in which said atypical Cms cytoplasm was derived through its female parent from a Mandarin cytoplasmic source, and in which said recessive genes $r_1r_1$ were derived through its male parent from a Dunfield germplasm base having an N cytoplasm and in which said recessive genes $r_2r_2$ additionally were derived through its male parent from a Tokyo germplasm base having an N cytoplasm.

34. A *Glycine max* seed product consisting of a substantially homogeneous binary admixture of seeds according to claim 33 wherein the (a) parent of said binary component (1) was derived through its female parent from the Elf variety, and in which said recessive genes $r_1r_1$ were derived through its male parent from the Bedford variety, and in which said recessive genes $r_2r_2$ additionally are derived through its male parent from the Braxton variety.

35. Plants of *Glycine max* which exhibit male sterility which is attributable to the combination of an atypical Cms cytoplasm and two distinct pairs of recessive genes $r_1r_1$ and $r_2r_2$.

36. Plants of *Glycine max* which exhibit male sterility according to claim 35 wherein said plants are present in a substantially uniform stand of at least 1000 plants.

37. Plants of *Glycine max* which exhibit male sterility according to claim 35 wherein said plants are the product of a controlled plant breeding program in which said atypical Cms cytoplasm was derived through the female parent from an appropriate cytoplasmic source, and in which said recessive genes $r_1r_1$ were derived through the male parent from a first gene source which possessed an N cytoplasm and said $r_1r_1$ genes, and in which said recessive genes $r_2r_2$ additionally were derived through the male parent from a second gene source which possessed an N cytoplasm and said $r_2r_2$ genes.

38. Plants of *Glycine max* which exhibit male sterility according to claim 35 wherein said plants are the product of a controlled plant breeding program in which said atypical Cms cytoplasm was derived through the female parent from a Mandarin cytoplasmic source, and in which said recessive genes $r_1r_1$ were derived through the male parent from a Dunfield germplasm base having an N cytoplasm and in which said recessive genes $r_2r_2$ additionally were derived through the male parent from a Tokyo germplasm base having an N cytoplasm.

39. Plants of *Glycine max* which exhibit male sterility according to claim 38 wherein said plants are the product of a controlled plant breeding program in which said atypical Cms cytoplasm was derived through the female parent from the Elf variety, and in which said recessive genes $r_1r_1$ were derived through the male parent from the Bedford variety, and in which said recessive genes $r_2r_2$ additionally were derived through the male parent from the Braxton variety.

40. Male fertile $F_1$ hybrid plants of *Glycine max* which are the result of a cross-pollination between (a) a male sterile female parent wherein the male sterility was attributable to the combination of an atypical Cms cytoplasm and two pairs of recessive genes $r_1r_1$ and $r_2r_2$, and (b) a male fertile male parent which possessed at least one pair of dominant genes selected from the group consisting of $R_1R_1$ and $R_2R_2$ which was capable of restoring male fertility to the progeny.

41. Male fertile $F_1$ hybrid plants of *Glycine max* according to claim 40 wherein said plants are present in a substantially uniform stand of at least one acre.

42. Male fertile $F_1$ hybrid plants of *Glycine max* according to claim 40 wherein said male sterile female parent (a) was formed via a controlled plant breeding program in which said atypical Cms cytoplasm was derived through its female parent from an appropriate cytoplasmic source, and in which said recessive genes $r_1r_1$ were derived through its male parent from a first gene source which possessed an N cytoplasm and said $r_1r_1$ genes, and in which said recessive genes $r_2r_2$ additionally were derived through its male parent from a second gene source which possessed an N cytoplasm and said $r_2r_2$ genes.

43. Male fertile $F_1$ hybrid plants of *Glycine max* according to claim 40 wherein said male sterile female parent (a) was formed via a controlled plant breeding program in which said atypical Cms cytoplasm was derived through its female parent from a Mandarin cytoplasmic source, and in which said recessive genes $r_1r_1$ were derived through its male parent from a Dunfield germplasm base having an N cytoplasm, and in which said recessive genes $r_2r_2$ additionally were derived through its male parent from a Tokyo germplasm base having an N cytoplasm.

44. Male fertile $F_1$ hybrid plants of *Glycine max* according to claim 43 wherein said male sterile female parent (a) was derived through its female parent from the Elf variety, and in which said recessive genes $r_1r_1$ were derived through its male parent from the Bedford variety, and in which said recessive genes $r_2r_2$ additionally are derived through its male parent from the Braxton variety.

45. A substantially uniform binary stand of *Glycine max* plants of at least one acre consisting of
  (1) male fertile $F_1$ hybrid soybean plants which were the result of cross-pollination between:
    (a) a male sterile female parent wherein the male sterility was attributable to the combination of an atypical Cms cytoplasm and two pairs of recessive genes $r_1r_1$ and $r_2r_2$, and
    (b) a male fertile male parent which possessed at least one pair of dominant genes selected from the group consisting of $R_1R_1$ and $R_2R_2$ which was capable of restoring male fertility to the offspring, and
  (2) male fertile soybean plants which were the result of the self-pollination of said male fertile parent (b) identified with respect to the binary component (1).

46. A substantially uniform binary stand of *Glycine max* plants according to claim 45 wherein the (a) parent of said binary component (1) was formed via a controlled plant breeding program in which said atypical Cms cytoplasm was derived through its female parent from an appropriate cytoplasmic source, and in which said recessive genes $r_1r_1$ were derived through its male parent from a first gene source which possessed an N cytoplasm and said $r_1r_1$ genes, and in which said recessive genes $r_2r_2$ additionally were derived through its male parent from a second gene source which possessed an N cytoplasm and said $r_2r_2$ genes.

47. A substantially uniform binary stand of *Glycine max* plants according to claim 45 wherein the (a) parent of said binary component (1) was formed via a controlled plant breeding program in which said atypical Cms cytoplasm was derived through its female parent from a Mandarin cytoplasmic source, and in which said recessive genes $r_1r_1$ were derived through its male parent from a Dunfield germplasm base having an N cytoplasm, and in which said recessive genes $r_2r_2$ additionally were derived through its male parent from a Tokyo germplasm base having an N cytoplasm.

48. A substantially uniform binary stand of *Glycine max* plants according to claim 47 wherein the (a) parent of said binary component (1) was derived through its female parent from the Elf variety, and in which said recessive genes $r_1r_1$ were derived through its male parent from the Bedford variety, and in which said recessive genes $r_2r_2$ additionally are derived through its male parent from the Braxton variety.

49. A process for the efficient production of seeds capable of growing male fertile $F_1$ hybrid *Glycine max* plants comprising:
(a) growing a substantially uniform population of male sterile soybean plants wherein said male sterility is attributable to the combination of an atypical Cms cytoplasm and two distinct pairs of recessive genes $r_1r_1$ and $r_2r_2$ in pollinating proximity to a substantially uniform population of male fertile soybean plants which possess at least one pair of dominant genes selected from the group consisting of $R_1R_1$ and $R_2R_2$ and which when crossed with said male sterile soybean plants enable the formation of seeds on said male sterile soybean plants which are capable of growing male fertile $F_1$ hybrid soybean plants, wherein with respect to said male sterile soybean plants said atypical Cms cytoplasm was derived through its female parent from an appropriate cytoplasmic source, and in which said recessive genes $r_1r_1$ were derived through its male parent from a first gene source which possessed said $r_1r_1$ genes, and in which said recessive genes $r_2r_2$ additionally were derived through its male parent from a second gene source which possessed said $r_2r_2$ genes,
(b) crossing said male sterile soybean plants and said male fertile soybean plants whereby seeds are formed on said male sterile soybean plants, and
(c) selectively recovering the seeds which have formed on said male sterile soybean plants.

50. A process for the efficient production of seeds capable of growing male fertile $F_1$ hybrid *Glycine max* plants according to claim 49 wherein with respect to said male sterile soybean plants said atypical Gms cytoplasm was derived through its female parent from a Mandarin cytoplasmic source, and in which said recessive genes $r_1r_1$ were derived through its male parent from a Dunfield germplasm base and in which said recessive genes $r_2r_2$ additionally were derived through its male parent from a Tokyo germplasm base.

51. A process for the efficient production of seeds capable of growing male fertile $F_1$ hybrid *Glycine max* plants according to claim 50 wherein with respect to said male sterile soybean plants said atypical Cms cytoplasm was derived through its female parent from the Elf variety, and in which said recessive genes $r_1r_1$ were derived through its male parent from the Bedford variety, and in which said recessive genes $r_2r_2$ additionally were derived through its male parent from the Braxton variety.

52. A process for the efficient production of seeds capable of growing male fertile $F_1$ hybrid *Glycine max* plants according to claim 49 wherein said substantially uniform populations of male sterile soybean plants and male fertile soybean plants are grown in alternating strips.

53. A process for the efficient production of seeds capable of growing male fertile $F_1$ hybrid *Glycine max* plants according to claim 49 which includes the additional step of selectively recovering seeds formed on said substantially uniform population of male fertile soybean plants grown in step (a).

54. A process for the efficient production of seeds capable of growing male fertile $F_1$ hybrid *Glycine max* plants according to claim 49 wherein said male fertile soybean plants grown in step (a) are a pure line variety.

55. A process for the efficient production of seeds capable of growing male fertile $F_1$ hybrid *Glycine max* plants according to claim 49 wherein said crossing of step (b) is carried out with the aid of pollen carrying insects.

56. A process for the efficient production of seeds capable of growing male sterile $F_1$ hybrid *Glycine max* plants according to claim 49 wherein said crossing of step (b) is carried out with the aid of pollen carrying bees.

57. A process for the efficient production of a substantially uniform binary seed blend containing a substantial proportion of seeds capable of growing male fertile $F_1$ hybrid *Glycine max* plants comprising:
(a) growing in a planting area a substantially random population of (i) male sterile soybean plants wherein said male sterility is attributable to the combination of an atypical Cms cytoplasm and two distinct pairs of recessive genes $r_1r_1$ and $r_2r_2$, and wherein said atypical Cms cytoplasm was derived through its female parent from an appropriate cytoplasmic source, and in which said recessive genes $r_1r_1$ were derived through its male parent from a first gene source which possessed said $r_1r_1$ genes, and in which said recessive genes $r_2r_2$ additionally were derived through its male parent from a second gene source which possessed said $r_2r_2$ genes, and (ii) male fertile soybean plants which possess at least one pair of dominant genes selected from the group consisting of $R_1R_1$ and $R_2R_2$ and which when crossed with said male sterile soybean plants enable the formation of seeds on said male sterile soybean plants which are capable of growing male fertile $F_1$ hybrid soybean plants,
(b) pollinating said substantially random population of soybean plants whereby seeds are formed on said male sterile plants which are capable of growing male fertile $F_1$ hybrid soybean plants and seeds are formed on said male fertile soybean plants as a result of self-pollination, and
(c) recovering seeds which have formed on said substantially random population of soybean plants growing in said planting area.

58. A process for the efficient production of a substantially uniform binary seed blend containing a substantial proportion of seeds capable of growing male fertile $F_1$ hybrid *Glycine max* plants according to claim 57 wherein said atypical Cms cytoplasm was derived through its female parent from a Mandarin cytoplasmic source, and in which said recessive genes $r_1r_1$ were derived through its male parent from a Dunfield germplasm base, and in which said recessive genes $r_2r_2$ additionally were derived through its male parent from a Tokyo germplasm base.

59. A process for the efficient production of a substantially uniform binary seed blend containing a substantial proportion of seeds capable of growing male fertile $F_1$ hybrid *Glycine max* plants according to claim 58 wherein with respect to said male sterile soybean plants of said substantially random population said atypical Cms cytoplasm was derived through its female parent from the Elf variety, and in which said recessive genes $r_1r_1$ were derived through its male parent from the Bedford variety, and in which said recessive genes $r_2r_2$ additionally were derived through its male parent from the Braxton variety.

60. A process for the efficient production of a substantially uniform binary seed blend containing a substantial proportion of seeds capable of growing male fertile $F_1$ hybrid *Glycine max* plants according to claim 57 wherein said male fertile soybean plants of said substantially random population are a pure line variety.

61. A process for the efficient production of a substantially uniform binary seed blend containing a substantial proportion of seeds capable of growing male fertile $F_1$ hybrid *Glycine max* plants according to claim 57 wherein said pollinating of step (b) is carried out with the aid of pollen carrying insects.

62. A process for the efficient production of a substantially uniform binary seed blend containing a substantial proportion of seeds capable of growing male fertile $F_1$ hybrid *Glycine max* plants according to claim 57 wherein said pollinating step (b) is carried out with the aid of pollen carrying bees.

63. A process for maintaining male sterile *Glycine max* plants useful in the production of male fertile $F_1$ hybrid soybean plants comprising:
 (a) growing a substantially uniform population of male sterile soybean plants wherein said male sterility is attributable to the combination of an atypical Cms cytoplasm and two distinct pairs of recessive genes $r_1r_1$ and $r_2r_2$ in pollinating proximity to a substantially uniform population of male fertile soybean plants which possess an N cytoplasm and two distinct pairs of recessive genes $r_1r_1$ and $r_2r_2$, wherein with respect to said male sterile soybean plants of said substantially uniform population said atypical Cms cytoplasm was derived through its female parent from an appropriate cytoplasmic source, and in which said recessive genes $r_1r_1$ were derived through its male parent from a first gene source which possessed said $r_1r_1$ genes, and in which said recessive genes $r_2r_2$ additionally were derived through its male parent from a second gene source which possessed said $r_2r_2$ genes,
 (b) crossing said male sterile soybean plants and said male fertile soybean plants whereby seeds are formed on said male sterile soybean plants which upon growth yield additional male sterile soybean plants, and
 (c) selectively recovering seeds which have formed on said substantially uniform population of male sterile soybean plants.

64. A process for maintaining male sterile *Glycine max* plants useful in the production of male fertile $F_1$ hybrid soybean plants according to claim 63 wherein with respect to said male sterile soybean plants of said substantially uniform population of step (a) said atypical Cms cytoplasm was derived through its female parent from a Mandarin cytoplasmic source, and in which said recessive genes $r_1r_1$ were derived through its male parent from a Dunfield germplasm base, and in which said recessive genes $r_2r_2$ additionally were derived through its male parent from a Tokyo germplasm base.

65. A process for maintaining male sterile *Glycine max* plants useful in the production of male fertile $F_1$ hybrid soybean plants according to claim 64 wherein with respect to said male sterile soybean plants of said substantially uniform population of step (a) said atypical Cms cytoplasm was derived through its female parent from the Elf variety, and in which said recessive genes $r_1r_1$ were derived through its male parent from the Bedford variety, and in which recessive genes $r_2r_2$ additionally were derived through its male parent from the Braxton variety.

66. A process for maintaining male sterile *Glycine max* plants useful in the production of male fertile $F_1$ hybrid soybean plants according to claim 63 wherein said crossing of step (b) is carried out with the aid of pollen carrying insects.

67. A process for maintaining male sterile *Glycine max* plants useful in the production of male fertile $F_1$ hybrid soybean plants according to claim 63 wherein said crossing of step (b) is carried out with the aid of pollen carrying bees.

68. A *Glycine max* seed product consisting of a substantially homogeneous assemblage of seeds which upon growth yield male sterile soybean plants wherein said male sterility is attributable to the combination of an atypical Cms cytoplasm and two distinct pairs of recessive genes $r_1r_1$ and $r_2r_2$, wherein said seed product was formed via a controlled plant breeding program in which said atypical Cms cytoplasm was derived through the female parent from an appropriate cytoplasmic source, and in which said recessive genes $r_1r_1$ were derived through the male parent from a first gene source which possessed said $r_1r_1$ genes, and in which said recessive genes $r_2r_2$ additionally were derived through the male parent from a second gene source which possessed said $r_2r_2$ genes.

69. A *Glycine max* seed product consisting of a substantially homogeneous assemblage of seeds which upon growth yield male sterile soybean plants according to claim 68, wherein said seed product was formed via a controlled plant breeding program in which said atypical Cms cytoplasm was derived through the female parent from a Mandarin cytoplasmic source, and in which said recessive genes $r_1r_1$ were derived through the male parent from a Dunfield germplasm base, and in which said recessive genes $r_2$ $r_2$ additionally were derived through the male parent from a Tokyo germplasm base.

70. A *Glycine max* seed product consisting of a substantially homogeneous assemblage of seeds which upon growth yield male sterile soybean plants according to claim 69, wherein said seed product was formed via a controlled plant breeding program in which said atypical Cms cytoplasm was derived through the female parent from the Elf variety, and in which said recessive genes $r_1r_1$ were derived through the male parent from the Bedford variety, and in which said recessive genes $r_2r_2$ additionally were derived through the male parent from the Braxton variety.

71. A *Glycine max* seed product consisting of a substantially homogenous assemblage of seeds which upon growth yield male fertile $F_1$ hybrid soybean plants which was the result of a cross-pollination between (a) a male sterile female parent wherein the male sterility was attributable to the combination of an atypical Cms cytoplasm and two pairs of recessive genes $r_1r_1$ and $r_2r_2$, and (b) a male fertile parent which possessed at least one pair of dominant genes selected from the group consisting of $R_1R_1$ and $R_2R_2$ which was capable of restoring male fertility to the progeny, wherein said male sterile female parent (a) was formed via a controlled plant breeding program in which said atypical Cms cytoplasm was derived through its female parent from an appropriate cytoplasmic source, and in which said recessive genes $r_1r_1$ were derived through its male parent from a first gene source which possessed said $r_1r_1$ genes, and in which said recessive genes $r_2r_2$ additionally were derived through its male parent from a second gene source which possessed said $r_2r_2$ genes.

72. A *Glycine max* seed product consisting of a substantially homogeneous assemblage of seeds which upon growth yield male fertile $F_1$ hybrid soybean plants according to claim 71 wherein said male sterile female parent (a) was formed via a controlled plant breeding program in which said atypical Cms cytoplasm was derived through its female parent from a Mandarin cytoplasmic source, and in which said recessive genes $r_1r_1$ were derived through its male parent from a Dunfield germplasm base, and in which said recessive genes $r_2r_2$ additionally were derived through its male parent from a Tokyo germplasm base.

73. A *Glycine max* seed product consisting of a substantially homogeneous assemblage of seeds which upon growth yield male fertile $F_1$ hybrid soybean plants according to claim 72 wherein said male sterile female parent (a) was derived through its female parent from the Elf variety, and in which said recessive genes $r_1r_1$ were derived through its male parent from the Bedford variety, and in which said recessive genes $r_2r_2$ additionally are derived through its male parent from the Braxton variety.

74. A *Glycine max* seed product consisting of a substantially homogeneous binary admixture of seeds which upon growth yield:

(1) male fertile $F_1$ hybrid soybean plants which were the result of cross-pollination between:

(a) a male sterile female parent wherein the male sterility was attributable to the combination of an atypical Cms cytoplasm and two pairs of recessive genes $r_1r_1$ and $r_2r_2$, and wherein said parent was formed via a controlled plant breeding program in which said atypical Cms cytoplasm was derived through its female parent from an appropriate cytoplasmic source, and in which said recessive genes $r_1r_1$ were derived through its male parent from a first gene source which possessed said $r_1r_1$ genes, and in which said recessive genes $r_2r_2$ additionally were derived through its male parent from a second gene source which possessed said $r_2r_2$ genes, and (b) a male fertile male parent which possessed at least one pair of dominant genes selected from the group consisting of $R_1R_1$ and $R_2R_2$ which was capable of restoring male fertility to the offspring, and (2) male fertile soybean plants which were the result of the self-pollination of said male fertile male parent (b) identified with respect to binary component (1).

75. A *Glycine max* seed product consisting of a substantially homogeneous binary admixture of seeds according to claim 74 wherein the (a) parent of said binary component (1) was formed via a controlled plant breeding program in which said atypical Cms cytoplasm was derived through its female parent from a Mandarin cytoplasmic source, and in which said recessive genes $r_1r_1$ were derived through its male parent from a Dunfield germplasm base and in which said recessive genes $r_2r_2$ additionally were derived through its male parent from a Tokyo germplasm base.

76. A *Glycine max* seed product consisting of a substantially homogeneous binary admixture of seeds according to claim 75 wherein the (a) parent of said binary component (1) was derived through its female parent from the Elf variety, and in which said recessive genes $r_1r_1$ were derived through its male parent from the Bedford variety, and in which said recessive genes $r_2r_2$ additionally were derived through its male parent from the Braxton variety.

77. Plants of *Glycine max* which exhibit male sterility which is attributable to the combination of an atypical Cms cytoplasm and two distinct pairs of recessive genes $r_1r_1$ and $r_2r_2$, wherein said plants are the product of a controlled plant breeding program in which said atypical Cms cytoplasm was derived through the female parent from an appropriate cytoplasmic source, and in which said recessive genes $r_1r_1$ were derived through the male parent from a first gene source which possessed said $r_1r_1$ genes, and in which said recessive genes $r_2r_2$ additionally were derived through the male parent from a second gene source which possessed said $r_2r_2$ genes.

78. Plants of *Glycine max* which exhibit male sterility according to claim 77 wherein said plants are the product of a controlled plant breeding program in which said atypical Cms cytoplasm was derived through the female parent from a Mandarin cytoplasmic source, and in which said recessive genes $r_1r_1$ were derived through the male parent from a Dunfield germplasm base and in which said recessive genes $r_2r_2$ additionally were derived through the male parent from a Tokyo germplasm base.

79. Plants of *Glycine max* which exhibit male sterility according to claim 78 wherein said plants are the product of a controlled plant breeding program in which said atypical Cms cytoplasm was derived through the female parent from the Elf variety, and in which said recessive genes $r_1r_1$ were derived through the male parent from the Bedford variety, and in which said recessive genes $r_2r_2$ additionally were derived through the male parent from the Braxton variety.

80. Male fertile $F_1$ hybrid plants of *Glycine max* which are the result of a cross-pollination between (a) a male sterile female parent wherein the male sterility was attributable to the combination of an atypical Cms cytoplasm and two pairs of recessive genes $r_1r_1$ and $r_2r_2$ and wherein said parent was formed via a controlled plant breeding program in which said atypical Cms cytoplasm was derived through its female parent from an appropriate cytoplasmic source, and in which said recessive genes $r_1r_1$ were derived through its male parent from a first gene source which possessed said $r_1r_1$ genes, and in which said recessive genes $r_2r_2$ additionally were derived through its male parent from a second gene source which possessed said $r_2r_2$ genes, and (b) a male fertile male parent which possessed at least one pair of dominant genes selected from the group consisting of $R_1R_1$ and $R_2R_2$ which was capable of restoring male fertility to the progeny.

81. Male fertility $F_1$ hybrid plants of *Glycine max* according to claim 80 wherein said plants are present in a substantially uniform stand of at least one acre.

82. Male fertility $F_1$ hybrid plants of *Glycine max* according to claim 80 wherein said male sterile female parent (a) was formed via a controlled plant breeding program in which said atypical Cms cytoplasm was derived through its female parent from a Mandarin cytoplasmic source, and in which said recessive genes $r_1r_1$ were derived through its male parent from a Dunfield germplasm base, and in which said recessive genes $r_2r_2$ additionally were derived through its male parent from a Tokyo germplasm base.

83. Male fertile $F_1$ hybrid plants of *Glycine max* according to claim 82 wherein said male sterile parent (a) was derived through its female parent from the Elf variety, and in which said recessive genes $r_1r_1$ were derived through its male parent from the Bedford variety, and in which said recessive genes $r_2r_2$ additionally are derived through its male parent from the Braxton variety.

84. A substantially uniform binary stand of *Glycine max* plants of at least one acre consisting of
   (1) male fertile $F_1$ hybrid soybean plants which were the result of cross-pollination between:
   (a) a male sterile female parent wherein the male sterility was attributable to the combination of an atypical Cms cytoplasm and two pairs of recessive genes $r_1r_1$ and $r_2r_2$, and wherein said parent was formed via a controlled plant breeding program in which said atypical Cms cytoplasm was derived through its female parent from an appropriate cytoplasmic source, and in which said recessive genes $r_1r_1$ were derived through its male parent from a first gene source which possessed said $r_1r_1$ genes, and in which said recessive genes $r_2r_2$ additionally were derived through its male parent from a second gene source which possessed said $r_2r_2$ genes, and
   (b) a male fertile male parent which possessed at least one pair of dominant genes selected from the group consisting of $R_1R_1$ and $R_2R_2$ which was capable of restoring male fertility to the offspring, and
   (2) male fertile soybean plants which were the result of the self-pollination of said male fertile patent (b) identified with respect to the binary component (1).

85. A substantially uniform binary stand of *Glycine max* plants according to claim 84 wherein the (a) parent of said binary component (1) was formed via a controlled plant breeding program in which said atypical Cms cytoplasm was derived through its female parent from a Mandarin cytoplasmic source, and in which said recessive genes $r_1r_1$ were derived through its male parent from a Dunfield germplasm base, and in which said recessive genes $r_2r_2$ additionally were derived through its male parent from a Tokyo germplasm base.

86. A substantially uniform binary stand of *Glycine max* plants according to claim 84 wherein the (a) parent of said binary component (1) was derived through its female parent from the Elf variety, and in which said recessive genes $r_1r_1$ were derived through its male parent from the Bedford variety, and in which said recessive genes $r_2r_2$ additionally are derived through its male parent from the Braxton variety.

* * * * *

UNITED STATES PATENT AND TRADEMARK OFFICE
CERTIFICATE OF CORRECTION

PATENT NO. : 4,545,146

DATED : October 8, 1985

INVENTOR(S) : William H. Davis

It is certified that error appears in the above-identified patent and that said Letters Patent is hereby corrected as shown below:

Col. 2, line 35, after "determined by" insert -- nuclear genes (Brim and Young, 1971). Therefore --.

Col. 4, line 24, after "soybeans" insert a period -- . --.

Col. 15, line 40, delete "of" and insert -- to --.

Col. 18, line 39, delete "form" and insert -- from --.

Col. 21, line 54, delete "Gms" and insert -- Cms --.

Col. 25, lines 45 to 62, indent in same manner as at Col. 18, lines 48 to 56.

Col. 27, line 1, delete "fertility" and insert -- fertile --.

Col. 27, line 4, delete "fertility" and insert -- fertile --.

Col. 27, line 26, to Col. 28, line 10, indent in same manner as at Col. 20, lines 45 to 53.

Signed and Sealed this

Seventh Day of January 1986

[SEAL]

Attest:

DONALD J. QUIGG

Attesting Officer     Commissioner of Patents and Trademarks